(12) United States Patent
Bristow

(10) Patent No.: US 9,643,991 B2
(45) Date of Patent: *May 9, 2017

(54) PROCESS FOR PREPARING A NOVEL CRYSTALLINE FORM OF EMAMECTIN BENZOATE AND USE THE SAME

(71) Applicant: ROTAM AGROCHEM INTERNATIONAL CO., LTD, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 50 days.

This patent is subject to a terminal disclaimer.

(21) Appl. No.: 14/733,054

(22) Filed: Jun. 8, 2015

(65) Prior Publication Data

US 2016/0355538 A1    Dec. 8, 2016

(51) Int. Cl.
*A01N 43/90* (2006.01)
*C07H 17/08* (2006.01)

(52) U.S. Cl.
CPC ............ *C07H 17/08* (2013.01); *A01N 43/90* (2013.01)

(58) Field of Classification Search
None
See application file for complete search history.

(56) References Cited

U.S. PATENT DOCUMENTS

| 4,874,749 | A | 10/1989 | Mrozik |
| 5,288,710 | A | 2/1994 | Cvetovich |
| 6,486,195 | B1 | 11/2002 | Cvetovich |

FOREIGN PATENT DOCUMENTS

FR    WO 9925187 A2 *    5/1999    ............ A01N 43/90

OTHER PUBLICATIONS

Braun, Crystal Growth & Design, 2011, vol. 11, 210-220.*
Boldyreva, Polymorphism of glycine. Thermodynamic and structural aspects, 2004.*

* cited by examiner

*Primary Examiner* — Layla Berry
(74) *Attorney, Agent, or Firm* — Dickinson Wright PLLC

(57) ABSTRACT

A crystalline modification V of emamectin benzoate, exhibiting at least 3 of the following reflexes in an X-ray powder diffractogram recorded using Cu—Kα radiation at 25° C.:

$2\theta = 4.34 \pm 0.2$ (1)

$2\theta = 10.58 \pm 0.2$ (2)

$2\theta = 12.32 \pm 0.2$ (3)

$2\theta = 15.19 \pm 0.2$ (4)

$2\theta = 18.57 \pm 0.2$ (5)

$2\theta = 20.41 \pm 0.2$ (6)

A process for the preparation of emamectin benzoate in the aforementioned form comprises i) preparing a solution of a solid form of emamectin benzoate in a solvent comprising ethyl acetate and n-hexane; ii) effecting crystallization of emamectin benzoate from the solution; and iii) isolating the emamectin benzoate formed. The crystalline modification V can be formulated to any suitable pesticidal formulations.

21 Claims, 3 Drawing Sheets

PROCESS FOR PREPARING A NOVEL CRYSTALLINE FORM OF EMAMECTIN BENZOATE AND USE THE SAME

BACKGROUND

1. Field

The present disclosure relates to a novel crystalline polymorph of 4"-deoxy-4"-epi-methylamino avermectin $B_{1a}/B_{1b}$ (emamectin benzoate), to processes for its preparation and to its use in agrochemical preparations.

2. Description of Related Art

Emamectin benzoate (4"-deoxy-4"-epi-methylamino avermectin $B_{1a}/B_{1b}$) is an insecticide with potent efficacy against pests, such as thrips, leafminers and worm pests, including alfalfa caterpillar, beet armyworm, cabbage looper, corn earworm, cutworm, diamondback moth, tobacco budworm, tomato fruitworm and tomato pinworm. Emamectin benzoate is described in U.S. Pat. No. 4,874,749 and in Cvetovich, R. J. et al, J. Organic Chem. 59:7704-7708, 1994.

U.S. Pat. No. 5,288,710 suggests that salts of emamectin are valuable agrochemicals. These salts are effective pesticides especially for combating insects and representatives of the order Acarina. Emamectin benzoate can combat pests listed in EP-A 736,252.

Emamectin benzoate is an efficient semi-synthetic antibiotic pesticide synthesized from the fermentation product avermectin B1. It is ultra-efficient, residue-free and pollution-free with a low toxicity (and can be formulated into nearly non-toxic formulations). Comparing the biological characteristics of emamectin benzoate with those of other avermectin pesticides, such as abamectin, doramectin, ivermectin, its insecticidal activity is higher by 1-3 orders of magnitude. It provides strong activity against Lepidoptera pole larvae and many other pests by both stomach poisoning and contact poisoning. It is effective at very low doses (0.084-2 g/ha) and has no adverse effects on beneficial insects, which makes it advantageous for integrated pest control. In addition, it expands the insecticidal spectrum and reduces the toxicity thereof to humans and animals.

Emamectin benzoate has superior activity to many other pesticides. It is especially ultra-efficient against pests of Lepidoptera and Diptera such as red tape leaf roller, *Aphidius* armyworm, cotton bollworm, tobacco hornworm, diamondback moth armyworm, beet armyworm, *Spodoptera* dryland greed, divergent pattern armyworm, cabbage looper, cabbage butterfly, cabbage moth, cabbage moth bar, tomato hornworm, potato beetles, Mexico ladybugs, etc.

Emamectin benzoate has the molecular formulae $C_{56}H_{81}NO_{15}$ ($B_{1a}$) and $C_{55}H_{79}NO_{15}$ ($B_{1b}$), and has molecular weights of 1008.3 ($B_{1a}$) and 994.2 ($B_{1b}$) respectively. Emamectin benzoate is a white or almost white crystalline powder with a melting point of 141-146° C. Emamectin benzoate is soluble in acetone, ethanol and methanol, slightly soluble in water, and insoluble in hexane. It is stable at a pH range of 5.0-7.0. Its chemical structural is:

R = Me or Et

Emamectin benzoate is known to exist in a number of polymorphic crystalline forms. U.S. Pat. No. 6,486,195 discloses four polymorphic or pseudomorphic forms of emamectin benzoate. However, these polymorphic forms have been found to be undesirable formulating into products because of residue formed after diluting the formulated products which may block the spraying filters easily. Therefore, there is a high demand to develop a new polymorphic form of emamectin benzoate which is suitable for preparing as a commercial formulation.

SUMMARY

To attempt to resolve some or all of the problems with existing crystalline modifications of emamectin benzoate, a new crystalline polymorphic form of emamectin benzoate has been prepared.

An embodiment of the invention relates to a novel crystalline polymorph of 4"-deoxy-4"-epi-methylamino avermectin $B_{1a}/B_{1b}$ (emamectin benzoate), to processes for its preparation, and to its use in agrochemical preparations.

It has been found that the crystalline polymorph of emamectin benzoate, termed crystalline modification V in the following, has a significant improvement in its stability. The crystalline modification V does not convert to other crystalline modifications even during prolonged storage. Furthermore, it has been found that the crystalline modification V is easier to be comminuted or ground compared to other crystalline modifications, and that formulations prepared using this modification are stable even after prolonged storage. This allows the preparation of suspension concentrates, oil-based suspension concentrates, water-dispersible granules and water-soluble granules. In addition, the crystalline modification V has a lower tendency to aggregate and recrystallize after dilution compared to the other crystalline modifications described in U.S. Pat. No. 6,486,195. For these reasons, the crystalline modification V is more suitable for preparing commercial formulations. By virtue of its stability, the crystalline modification V gives the desired long storage period to its formulations. Hence, it is possible to prepare formulations of emamectin benzoate with excellent stability using the crystalline modification V.

The crystalline modification V of emamectin benzoate is highly suitable for preparing compositions for controlling pests. Accordingly, another embodiment of the invention also provides compositions for controlling pests comprising the crystalline modification V of emamectin benzoate on its own, as a mixture with auxiliaries and carriers, and as a mixture with other active compounds, as well as methods for controlling pests by applying such compositions to a locus in need of such control, such as a plant or plant parts.

According to an embodiment of the invention, the crystalline modification V of emamectin benzoate can be obtained by the processes below:

Emamectin benzoate is dissolved and then crystallized from solvents. In the first aspect, the invention provides a process for preparing a crystalline modification V of emamectin benzoate comprising steps of:

i) preparing a solution of a solid form of emamectin benzoate in a solvent;

ii) effecting crystallization of emamectin benzoate from the solution; and iii) isolating the emamectin benzoate formed.

BRIEF DESCRIPTION OF DRAWINGS

The embodiments and aspects of the invention can be more clearly understood by reference to the following figures, which are intended to illustrate, not limit, the scope of the invention and the appended claims:

DETAILED DESCRIPTION OF SPECIFIC EMBODIMENTS

Various aspects of the invention can be more clearly understood by reference to the following disclosure of specific embodiments, which is intended to illustrate, not limit, the scope of the invention and the appended claims.

In an embodiment, the invention provides a crystalline modification V of emamectin benzoate, exhibiting at least 3 of the following reflexes in an X-ray powder diffractogram recorded using Cu—Kα radiation at 25° C.:

$2\theta = 4.34 \pm 0.2$ (1)

$2\theta = 10.58 \pm 0.2$ (2)

$2\theta = 12.32 \pm 0.2$ (3)

$2\theta = 15.19 \pm 0.2$ (4)

$2\theta = 18.57 \pm 0.2$ (5)

$2\theta = 20.41 \pm 0.2$ (6)

The polymorphic form of emamectin benzoate of an embodiment of the present invention is characterized by an X-ray powder diffractogram having at least three of the reflexes indicated above.

Figure 2:
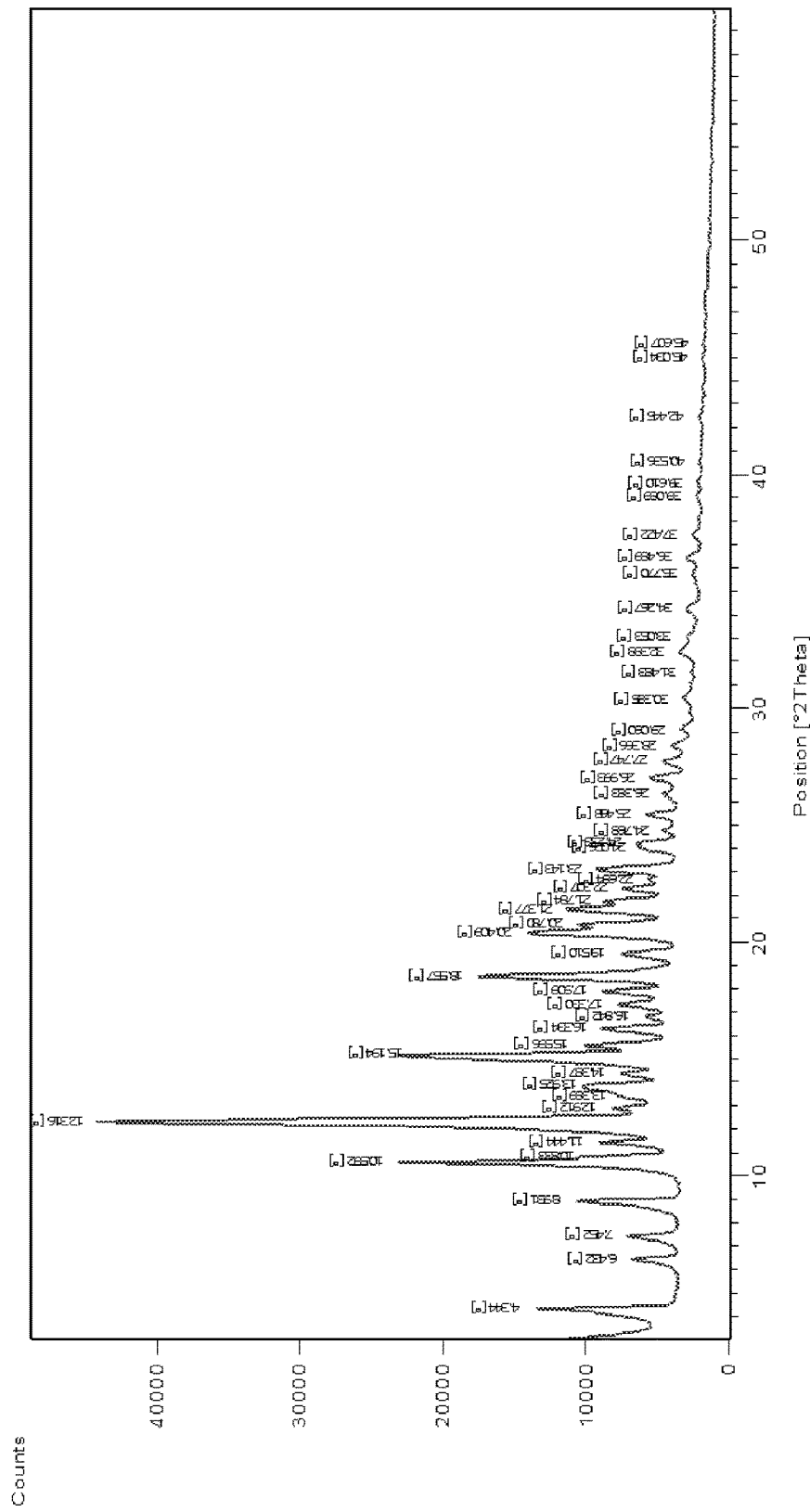
FIG. 2 is a graph showing an X-ray powder diffractograph of an embodiment of crystalline modification V of emamectin benzoate as described herein.

Preferably, the present polymorphic form is one having at least four of the aforementioned reflexes, more preferably at least five of the said reflexes. A particularly preferred form of emamectin benzoate is one with an X-ray powder diffractogram having all six of the reflexes indicated above. An X-ray powder diffractogram of the crystalline modification V of emamectin benzoate is shown in FIG. 2, as described in detail hereinafter. Preferably the present polymorphic form is one having at least the reflexes (2), (3), (4) and (5). Other particular embodiments include those where the polymorphic form includes at least the reflexes (1), (2), and (3), or those where the polymorphic form includes at least the reflexes (2), (3), and (4), or at least the reflexes (3), (4) and (5), or at least the reflexes (2), (3), and (5), or at least the reflexes (2), (4), and (5). Other particular embodiments include those where the polymorphic form includes any of the above reflexes, along with the reflexes at (1), or (6) or both.

Figure 1:
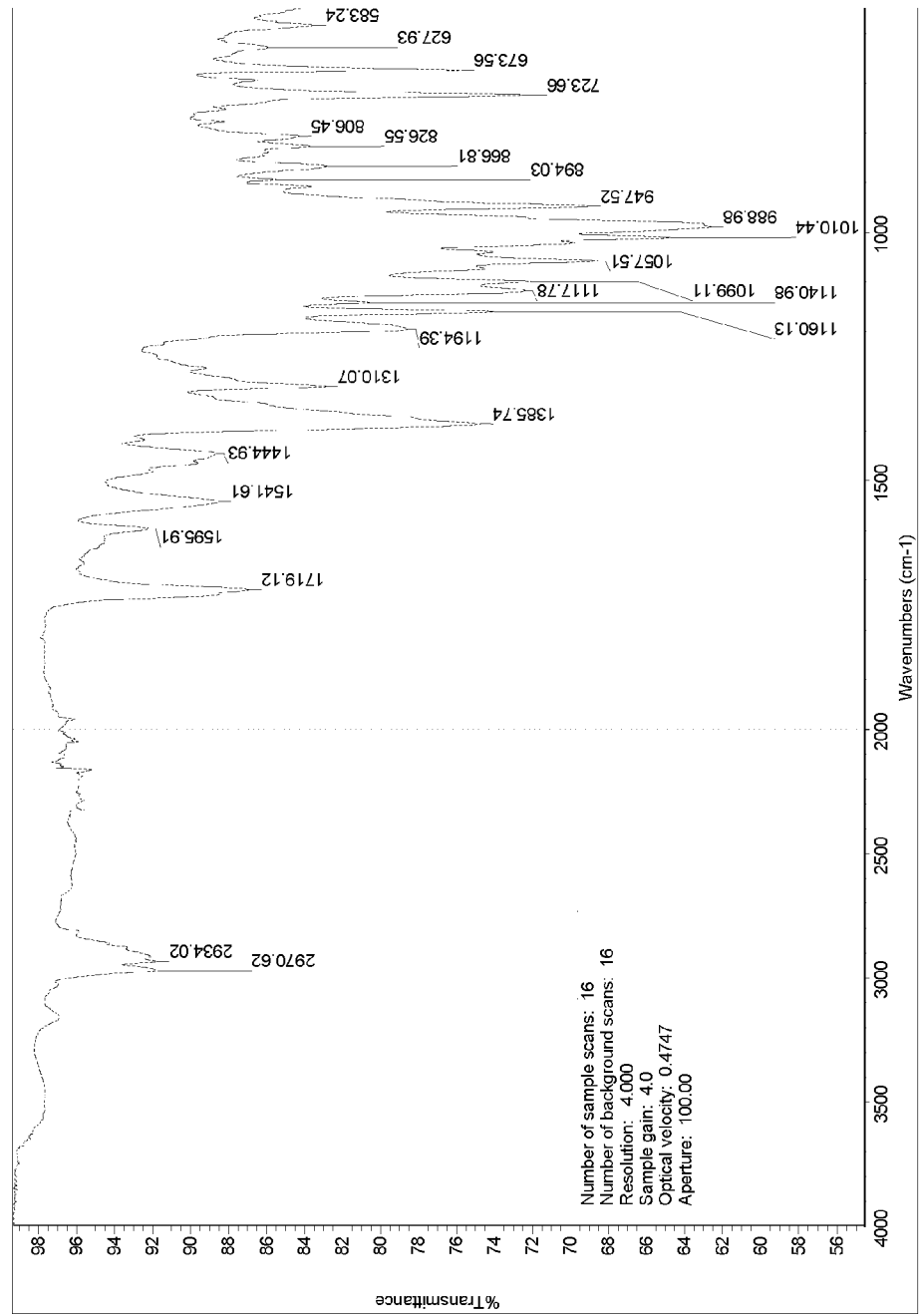
FIG. 1 is a graph showing an infrared (IR) spectra of an embodiment of crystalline modification V of emamectin benzoate as described herein.

The x-ray diffractogram was determined using the following parameters:

Philips automated powder diffractometer model 3600-02
Theta compensating slit and graphite monochromator
Copper (K-alpha) radiation, 40 kV, 30 mA
Step size: 0.03 degree 2-theta
Count time: 1.0 second
Maximum peak intensity: 1989 counts per second
Scan range: 2-60 degrees 2-theta The crystalline modification V of emamectin benzoate according to an embodiment of the invention may be further characterized by IR spectroscopy. The IR spectrum is shown in FIG. 1 with characteristic bands at 2970.62 cm$^{-1}$ and 2934.02 cm$^{-1}$.

All IR spectra were obtained using the following acquisition parameters:

| FT-IR spectrometer | Bruker Tensor37 |
|---|---|
| Diamond ATR unit | from Specac |
| Wavelength range | 550-4000 cm$^{-1}$ |
| Resolution | 4 cm$^{-1}$ |
| Number of scans | 16 |

Figure 3:
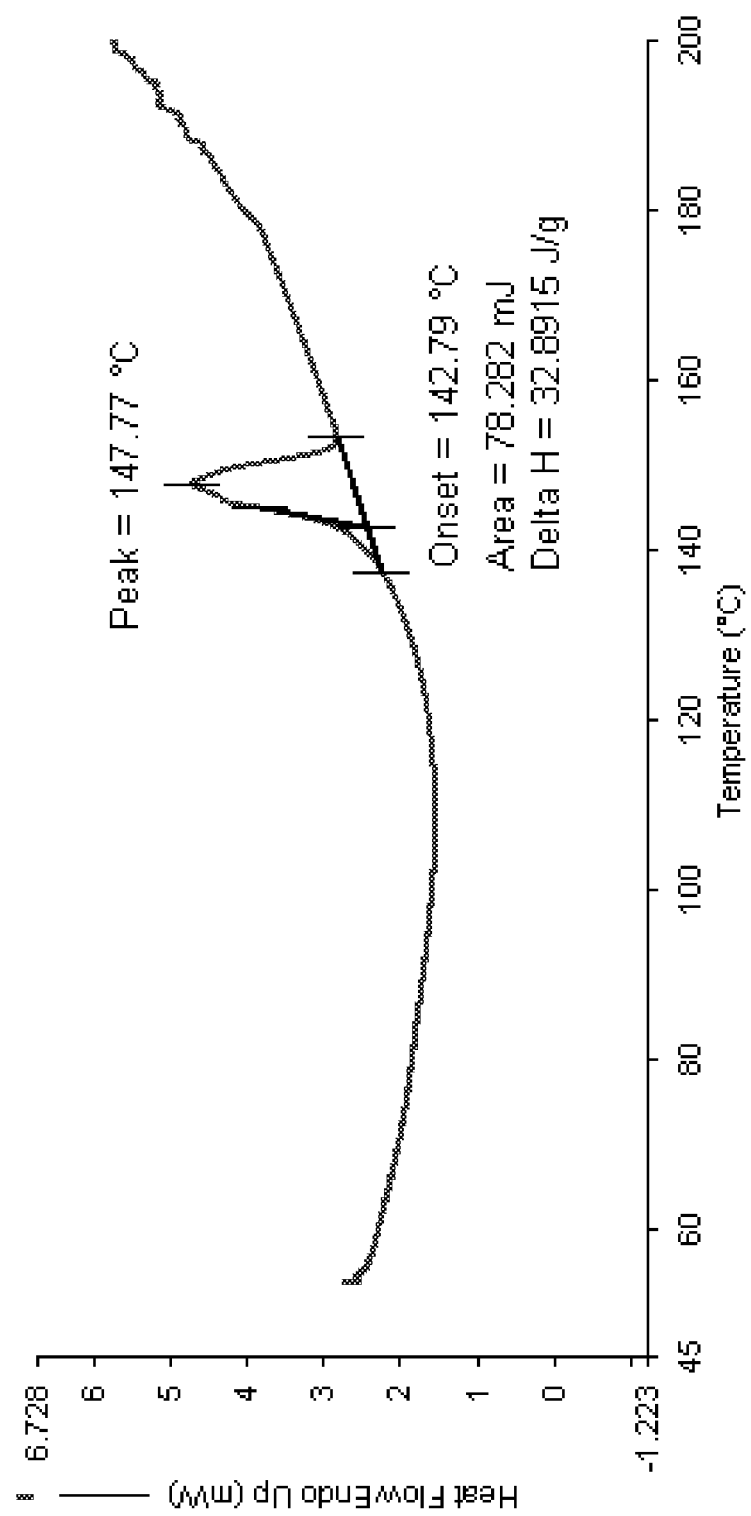
FIG. 3 is a graph showing the results of differential scanning calorimetry (DSC) on an embodiment of crystalline modification V of emamectin benzoate as described herein.

The crystalline modification V of emamectin benzoate according to the invention may be further characterized by differential scanning calorimetry (DSC) (FIG. 3). The crystalline modification V of emamectin tested contain no water, i.e., anhydrate. A major melting endotherm with peak temperature of 147.77° C., extrapolated onset temperature of 142.79° C. with an associated heat of 32.89 J/g.

All thermal data were collected on a Model 1090 Thermal Analyzer from ambient to 200° C. The Model 1090 was connected to a Model 910 DSC Module for the differential scanning calorimetry experiments. The DSC Module was purged with nitrogen during the course of the experiments. Prior to the experiments, the DSC Module was calibrated using pure indium.

For the DSC work, approximately 2 mg of each sample was hermetically sealed into a coated aluminum sample pan. The sample was then heated from ambient to 200° C. at a rate of 5° C./minute. Following each scan, the data was plotted and analyzed using the 1090 General Analysis program (v1.0). The analysis was repeated 3 times using different samples for each run.

Methods for preparing emamectin benzoate are known in the art. Emamectin benzoate is manufactured and available on a commercial scale. A method for preparing emamectin benzoate is described in U.S. Pat. No. 5,288,710. Emamectin benzoate prepared according to such processes can then be subjected to a crystallization process from a solvent, as described in more detail below, in order to produce the crystalline modification V, according to an embodiment of the invention.

Suitable solvents can be halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane, white spirits with components having boiling points in the range, for example, of from 40° C. to 250° C., cymene, petroleum fractions within a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol).

Preferred solvents are ethers, aromatic hydrocarbons such as benzene, toluene, xylene, chlorobenzene, esters and aliphatic alcohols and mixtures thereof. Particularly preferred solvents or solvent mixtures are isopropanol, toluene, methyl-tetrahydrofuran, diethyl carbonate, chlorobenzene, n-butyl acetate, isobutyl acetate, n-butanol, ethanol, ethyl malonate, methyl t-butyl ether, and also mixtures of toluene and butanol, toluene and n-butyl acetate, ethyl malonate and methyl t-butyl ether, and butyl acetate and methyl t-butyl ether. Solvent mixtures of more than 2 components are also possible. In this invention, a mixture of ethyl acetate and n-hexane is highly preferred.

In a further aspect, the present invention provides a process for preparing a crystalline modification V of emamectin benzoate comprising steps of:
  i) preparing a solution of a solid form of emamectin benzoate in a solvent comprising a mixture of ethyl acetate and n-hexane;
  ii) effecting crystallization of emamectin benzoate from the solution; and
  iii) isolating the emamectin benzoate formed to obtain crystalline modification V emamectin benzoate.

In step (i), emamectin benzoate is dissolved in a solvent comprising ethyl acetate and n-hexane. The solvent may comprise other solvent components or may comprise essentially a combination of the aforementioned solvent components. In a preferred embodiment, the solvent consists essentially of a mixture of ethyl acetate and n-hexane.

Ethyl acetate and n-hexane may be present in the solvent in any suitable ratio. For example, the two solvent components may be present in a ratio of from 5:1 to 1:5, more preferably from 4:1 to 1:4. In one preferred embodiment, ethyl acetate and n-hexane are employed as the solvent components in a ratio of 1:4, more preferably in a ratio of about 1:3.5.

Emamectin benzoate is crystallized from the solution. Techniques for crystallizing emamectin benzoate from the solution can include, for example, in an embodiment where the solution is formed in step (i) at elevated temperatures, cooling the solution to room or ambient temperature at a speed allowing crystallization. In one preferred embodiment, crystallization is effected by concentrating the solution formed in step (i) of the process. Alternatively, or in addition thereto, seed crystals, in particular seed crystals of the aforementioned crystalline modification V of emamectin benzoate, may be added to the solution produced in step (i), to facilitate and enhance crystallization.

It is preferred that the solid of emamectin benzoate recovered during the crystallization stage is washed with a solvent one or more times. It is preferred that the solvent employed in the washing stage is one or more of the components of the solvent employed to form the solution in step (i), as described hereinbefore. N-Hexane is a particularly suitable solvent for washing the recovered solid of emamectin benzoate.

An embodiment of the invention also embraces compositions comprising the crystalline modification V of emamectin benzoate. Preference is given to using compositions comprising less than 20% by weight of emamectin benzoate, particularly preferably less than 15% by weight, very particularly preferably less than 10% by weight, especially preferably less than 6% by weight, most preferably is 4% or 5% by weight, of emamectin benzoate for the formulation.

The activity of emamectin benzoate as a pesticidal agent is known in the art and is used on a commercial scale. Emamectin benzoate in the crystalline modification V of the present invention finds use in the control of pests and pest infestations. Techniques of formulating and using emamectin benzoate are known in the art, for example as disclosed in the documents discussed hereinbefore. Emamectin benzoate in the crystalline modification V of an embodiment of the present invention may be formulated and applied in an analogous manner.

Accordingly, in a further aspect, the present invention provides a pesticidal composition comprising emamectin benzoate in the crystalline modification V as hereinbefore defined.

Accordingly, the invention furthermore provides processes for preparing compositions for controlling pests using the crystalline modification V of emamectin benzoate and compositions comprising the crystalline modification V of emamectin benzoate.

The crystalline modification V of emamectin benzoate can be converted in a known manner to the customary formulations, such as suspension concentrates, oil-based suspension concentrates, soluble granules, dispersible concentrates, emulsifiable concentrates (emulsion concentrates), emulsion seed dressings, suspension seed dressings, granules, microgranules, suspoemulsions, water-soluble granules, water-soluble concentrates and water-dispersible granules, using suitable auxiliaries and carriers or solvents. Here, the active compound should be present in a concentration of from about 0.1 to 20% by weight of the total mixture, i.e. in amounts sufficient to achieve the required dosage. The formulations are prepared, for example, by extending the crystalline modification V of emamectin benzoate with water, solvents and/or carriers, using, if appropriate, emulsifiers and/or dispersants, and/or other auxiliaries.

These formulations are prepared in a known manner by mixing the active compounds with customary additives, for example, customary extenders and also solvents or diluents, colorants, wetting agents, dispersants, emulsifiers, antifoams, thickeners and water.

Suitable extenders are, for example, water, polar and nonpolar organic chemical liquids, for example from the classes of aromatic and non-aromatic hydrocarbons (such as paraffins, alkylbenzenes, alkylnaphthalenes, chlorobenzenes), alcohols (such as methanol, ethanol) and polyols (which, if appropriate, may also be substituted, etherified and/or esterified), ketones (such as acetone, cyclohexanone), esters (including fats and oils), (poly)ethers, unsubstituted and substituted amines, amides, lactams (such as N-alkylpyrrolidones), lactones, sulphones, and sulphoxides (such as dimethyl sulphoxide). Preferred extender is tetrahydrofurfuryl alcohol.

In some embodiments, the wetting agent may comprise a nonionic surfactant. Such preferred nonionic surfactants include but not limited to alcohol oxyalkylates, alkyl phenol oxyalkylates, and nonionic esters (such as sorbitan esters and alkoxylates of sorbitan esters). Examples of suitable surfactants include but not limited to castor oil alkoxylates, fatty acid alkoxylates, lauryl alcohol alkoxylates, nonylphenol alkoxylates, octylphenol alkoxylates, tridecyl alcohol alkoxylates, such as POE-10 nonylphenol ethoxylate, POE-100 nonylphenol ethoxylate, POE-12 nonylphenol ethoxylate, POE-12 octylphenol ethoxylate, POE-12 tridecyl alcohol ethoxylate, POE-14 nonylphenol ethoxylate, POE-15 nonylphenol ethoxylate, POE-18 tridecyl alcohol ethoxylate, POE-20 nonylphenol ethoxylate, POE-20 oleyl alcohol ethoxylate, POE-20 stearic acid ethoxylate, POE-3 tridecyl alcohol ethoxylate, POE-30 nonylphenol ethoxylate, POE-30 octylphenol ethoxylate, POE-34 nonylphenol ethoxylate, POE-4 nonylphenol ethoxylate, POE-40 castor oil ethoxylate, POE-40 nonylphenol ethoxylate, POE-40 octylphenol ethoxylate, POE-50 nonylphenol ethoxylate, POE-50 tridecyl alcohol ethoxylate, POE-6 nonylphenol ethoxylate, POE-6 tridecyl alcohol ethoxylate, POE-8 nonylphenol ethoxylate, POE-9 octylphenol ethoxylate, mannide monooleate, sorbitan isostearate, sorbitan laurate, sorbitan monoisostearate, sorbitan monolaurate, sorbitan monooleate, sorbitan monopalmitate, sorbitan monostearate, sorbitan oleate, sorbitan palmitate, sorbitan sesquioleate, sorbitan stearate, sorbitan trioleate, sorbitan tristearate, POE-20 sorbitan monoisostearate ethoxylate, POE-20 sorbitan monolaurate ethoxylate, POE-20 sorbitan monooleate ethoxylate, POE-20 sorbitan monopalmitate ethoxylate, POE-20 sorbitan monostearate ethoxylate, POE-20 sorbitan trioleate ethoxylate, POE-20 sorbitan tristearate ethoxylate, POE-30 sorbitan tetraoleate ethoxylate, POE-40 sorbitan tetraoleate ethoxylate, POE-6 sorbitan hexastearate ethoxylate, POE-6 sorbitan monstearate ethoxylate, POE-6 sorbitan tetraoleate ethoxylate, and/or POE-60 sorbitan tetrastearate ethoxylate. Preferred nonionic surfactants include alcohol oxyalkyalates (such as POE-23 lauryl alcohol) and alkyl phenol ethoxylates (such as POE-20 nonyl phenyl ether). Other applicable nonionic surfactants are esters such as sorbitan monooleate. Preferred wetting agent is POE-20 sorbitan monostearate ethoxylate.

Suitable dispersants and/or emulsifiers that may be present in formulations containing crystalline modification V emamectin benzoate, in particular in the seed dressing formulations disclosed herein, which can be used according to the invention include all nonionic, anionic, and cationic dispersants which are customary in the formulation of active agrochemical compounds. With preference, it is possible to use nonionic or anionic dispersants, or mixtures of nonionic and anionic dispersants. Particularly suitable nonionic dispersants are ethylene oxide-propylene oxide block polymers, alkylphenol polyglycol ethers, tristyrylphenol polyglycol ethers, and their phosphated or sulphated derivatives, tristyrylphenol ethoxylates and vinyl acetate/vinylpyrrolidone copolymer. Particularly suitable anionic dispersants are lignosulphonates, polyacrylic salts, and arylsulphonate-formaldehyde condensates.

Suitable antifoaming agents that may be present in formulations containing crystalline modification V emamectin benzoate, in particular the seed dressing formulations disclosed herein, which can be used according to the invention include all foam-inhibiting substances which are customary in the formulation of active agrochemical compounds. With preference it is possible to use silicone defoamers and magnesium stearate.

Suitable thickeners that may be present in formulations containing crystalline modification V emamectin benzoate, in particular the seed dressing formulations which can be used according to the invention include all substances which can be used for such purposes in agrochemical compositions. Preferred suitability is possessed by cellulose derivatives, acrylic acid derivatives, xanthan, modified clays, and highly dispersed silica.

It is possible to use colorants such as inorganic pigments (for example iron oxide, titanium oxide and Prussian Blue), organic dyestuffs (such as FD&C Blue No. 1, alizarin dyestuffs, azo dyestuffs and metal phthalocyanine dyestuffs), and trace nutrients (such as salts of iron, manganese, boron, copper, cobalt, molybdenum and zinc). Preferred colorant is FD&C Blue No. 1.

The crystalline modification V emamectin benzoate as active compound according to the invention can be present in typical commercially available formulations and use forms for emamectin benzoate, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals). A mixture with other known active compounds (such as herbicides, fertilizers, growth regulators, safeners, semiochemicals, or with agents for improving plant properties) is also possible.

When used as insecticides, the crystalline modification V emamectin benzoate as according to the invention can furthermore be present in the commercially available formulations and use forms for emamectin benzoate, prepared from these formulations, and as a mixture with synergistic agents. Synergistic agents are compounds which increase the action of the active compounds, without it being necessary for the synergistic agent added to be active itself.

When used as insecticides, crystalline modification V emamectin benzoate as according to the invention can furthermore be present in the commercially available formulations and use forms for emamectin benzoate, prepared from these formulations, and as a mixture with inhibitors which reduce degradation of the active compound after its use in the environment of the plant, on the surface of plant parts or in plant tissues.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods including the transgenic plants and the plant cultivars which can or cannot be protected by plant breeders' rights. Plant parts are to be understood as meaning all parts and organs of plants above and below the ground, such as shoot, leaf, flower and root. Examples of which may be mentioned include leaves, needles, stalks, stems, flowers, fruit bodies, fruits, seeds, roots, tubers and rhizomes. The plant parts also include harvested material, and vegetative and generative propagation material such as cuttings, tubers, rhizomes, offshoots and seeds.

The present invention provides a use of a crystalline modification V of emamectin benzoate or the composition comprising the crystalline modification V of emamectin benzoate for combatting insects, nematodes and plant parasites.

The insects to be controlled include one or more selected from the group consisting of *Tribolium* sp., *Tenebrio* sp., (for stored grains), spider mites (*Tetranychus* sp.), aphids (*Acyrthiosiphon* sp.), migratory orthopterans, such as locusts and immature stages of insects living on plant tissue of agricultural plants, southern army worm and Mexican bean beetle larvae, pine coneworm (*Dioryctria* spp.), pine cone seed bug (suppression of *Leptoglossus* and *Tetyra* spp. in the year of treatment), aphid, bagworm, fall webworm, Japanese beetle, gypsy moth, mimosa webworm, oak, tussock moth, leafminers (such as Lepidoptera, coleoptera, pine needle scale, red palm mite, sawfly (such as elm, pine), tent caterpillars (such as Eastern, Forest, Pacific, and Western), western spruce, budworm, winter moth, flatheaded borers (such as adult and larvae of bronze birch borer, emerald ash borer and two-lined chestnut borer), clearwing borers (such as ash and sequoia pine pitch tube moth), ambrosia beetles, roundheaded borers (including asian longhorn beetles), scolytids (bark beetles) 1ps engraver beetles, mountain pine beetle, southern pine beetle, spruce beetle, western pine beetle, cynipid gall wasps including black oak gall, pinewood nematode, lilac borer, ash borer (*Podosesia syringae*). The nematodes and plant parasites are selected from the group consisting of *Meloidogyne* sp. and any species which may be of importance in agriculture.

Treatment according to the invention of the plants and plant parts with the active compounds is carried out by applying the active compounds, or formulations containing the active compounds, directly to the plants or plant parts, or by allowing the compounds to act on their surroundings, habitat or storage space. This application can be by the customary treatment methods. Examples of these customary treatment methods include dipping, spraying, vaporizing, fogging, broadcasting, painting on and in the case of propagation material, and applying one or more coats particularly in the case of seed.

Embodiments of the present invention will now be described by the following examples for illustrative purposes only.

EXAMPLE A

Preparation of Emamectin Benzoate

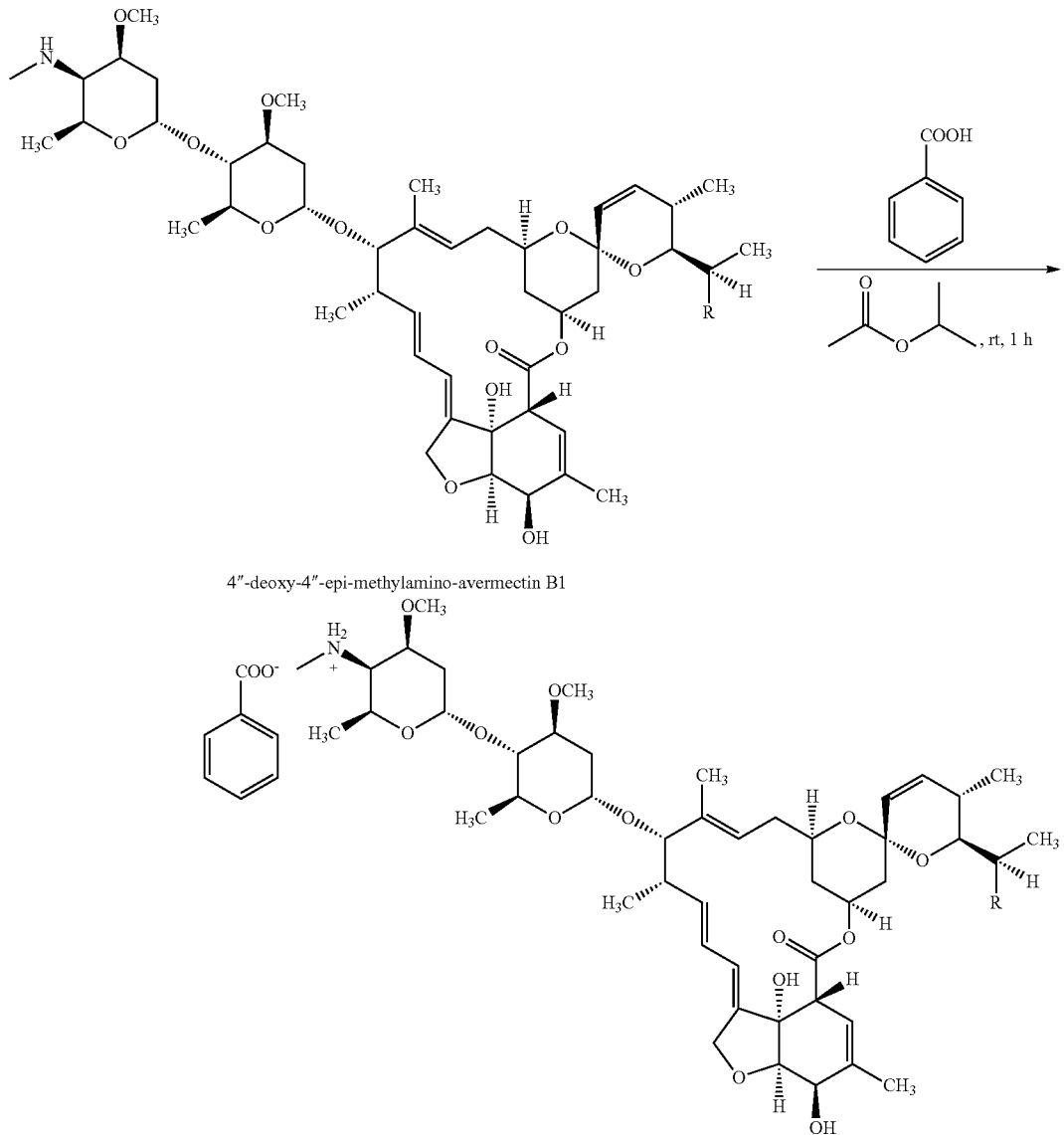

B1a: R = CH$_2$CH$_2$
B1b: R = CH$_3$ 6.4 kg benzoic acid under stirring was added to 52.5 kg 4"-deoxy -4"-epi- methylamino-avermectin B1 in 100 kg isopropyl acetate. The molar ratio is about 1.05:1. After stirring for 1 h, heat up to concentrate under reduced pressure. Control the temperature of heat medium less than 65° C. After removing most of the solvent, obtain about 60 kg foam-like yellow solid with the purity of 78%. The yield for this step is about 97%.

EXAMPLE 1

Preparation of the Crystalline Modification V of Emamectin Benzoate

Crystallization from Ethyl Acetate and n-hexane 88 kg (100 L) ethyl acetate was charged into the reactor to dissolve crude emamectin benzoate obtained in Example A, then 277 kg (350 L) n-hexane was dropped into the solution under stirring. This mixing process was continued for 2 hours under room temperature, until a white solid appeared. The mixture was then cooled down to a temperature of 0° C.-5° C. and maintained at this temperature for 1 hour to allow complete crystallization. After that, the mixture was centrifuged to obtain a filter cake, which was washed with additional n-hexane. The filtrate and wash solvent were combined, and then delivered to a waste solvent treatment system for necessary treatment with respect of local government requirement.

The filter cake was discharged and dried with a double-cone rotary vacuum dryer. The dryer and vacuum pump were started to allow the rotation to occur for 0.5 h at room temperature. Then, the temperature of the heating medium was increased and controlled at 65° C. After 1 h, the sample was taken out and weighed every 0.5 h. If the weights of two consecutive samples did not change, the filter cake was cooled down to room temperature. 41.9 kg of the final technical grade emamectin benzoate was obtained with a purity of 95%. The yield of this step was 85%.

IR spectroscopy of the final technical grade emamectin benzoate indicates bands at 2970.62 $cm^{-1}$ and 2934.02 $cm^{-1}$. The IR spectrum is indicated in FIG. 1.

The crystalline material obtained exhibits the X-ray powder diffractogram (FIG. 2) with the reflexes listed in Table 1 below:

TABLE 1

| Crystalline modification V | |
|---|---|
| 2 θ (°) | d (Å) |
| 4.34 ± 0.2 | 20.63 ± 0.05 |
| 10.58 ± 0.2 | 8.35 ± 0.03 |
| 12.32 ± 0.2 | 7.13 ± 0.03 |
| 15.19 ± 0.2 | 5.84 ± 0.02 |
| 18.57 ± 0.2 | 4.78 ± 0.02 |
| 20.41 ± 0.2 | 4.35 ± 0.02 |

The final technical grade emamectin benzoate (the crystalline modification V of emamectin benzoate) was further characterized by differential scanning calorimetry (DSC) (FIG. 3). The crystalline modification V of emamectin contain no water, i.e., anhydrate. A major melting endotherm with peak temperature of 147.77° C., extrapolated onset temperature of 142.79° C. with an associated heat of 32.89 J/g.

EXAMPLE 2

Preparation of Soluble Liquid (SL) Formulation

The components listed in Table 2 were mixed with stirring and dissolved at room temperature to obtain a homogeneous liquid. The crystalline modification V of emamectin benzoate was obtained from Example 1 above. Amounts of components were given in weight percent, based on the weight of the resulting formulation, unless otherwise indicated.

TABLE 2

| Content | Weight % | Function |
|---|---|---|
| Emamectin benzoate crystalline modification V, 95% | 4.21 | Active compound |
| Toximul ®SEE-341 | 1.00 | Wetting agent |
| FD&C Blue No. 1 | 0.02 | Dye |
| Tetrahydrofurfuryl alcohol | 75.00 | Solvent |
| Deionized Water (q.s.) | 19.77 | Filler |

EXAMPLE 3

Preparation of Emulsifiable Concentrate (EC) Formulation

The liquid components listed in Table 3 below were mixed with stirring at room temperature until a homogeneous liquid was obtained. The crystalline modification V of emamectin benzoate was obtained from Example 1 above. Solid components were dissolved in the liquid.

TABLE 3

| Content | Weights % | Function |
|---|---|---|
| Emamectin benzoate crystalline modification V, 95% | 4.21 | Active compound |
| Butylated hydroxytoluene (BHT) | 1.00 | Antioxidant |
| Paraffinic oil | 6.40 | Liquid carrier |
| POE 30 castor oil | 9.00 | Liquid carrier |
| Tristyrylphenol 54M ethoxylate (EMULSOGEN ®TS54) | 9.00 | Emulsifier |
| VP/VA copolymer (LUVITEC ®VA 64 from BASF) | 18.00 | Dispersant |
| 1-Hexanol | 52.39 | Solvent |

EXAMPLE 4

Preparation of Suspension Concentrate (SC) Formulation

The liquid components listed in Table 4 below were mixed with stirring at room temperature until a homogeneous liquid was obtained. The crystalline modification V of emamectin benzoate was obtained from Example 1 above. Solid components were dissolved in the liquid.

TABLE 4

| Content | Weights % | Function |
|---|---|---|
| Emamectin benzoate crystalline modification V, 95% | 4.21 | Active compound |
| Tristyrylphenol 54M ethoxylate (EMULSOGEN ® TS54) | 9.00 | Emulsifier |

TABLE 4-continued

| Content | Weights % | Function |
|---|---|---|
| VP/VA copolymer (LUVITEC ® VA 64 from BASF) | 2.00 | Emulsifier |
| Sodium N-methyl N-oleyl aturate | 9.00 | Surfactant |
| Sodium alkyl naphalene sulonate | 18.00 | Surfactant |
| Alkylpolyvinylpyrrolidone | 2.00 | Thickening agent |
| Butylated hydroxytoluene (BHT) | 1.00 | Antioxidant |
| Water | 59.00 | Filler |

EXAMPLE 5

Preparation of Soluble Granules (SG)

The liquid components listed in Table 5 below were mixed with stirring at room temperature until a homogeneous liquid was obtained. The crystalline modification V of emamectin benzoate was obtained from Example 1 above. Solid components were dissolved in the liquid.

TABLE 5

| Content | Weights % | Function |
|---|---|---|
| Emamectin benzoate crystalline modification V, 95% | 5.26 | Active compound |
| 2,6-Di-tert-butyl-4-methylphenol | 3.00 | Antioxidant |
| Sodium dodecyl sulfate | 10.00 | Surfactant |
| Sodium methylenedinaphalene disulphonate | 5.00 | Surfactant |
| Fatty alcohol-polyoxyethylene ether | 4.00 | Surfactant |
| Lactose | 72.74 | Filler |

EXAMPLE 6

Preparation of Soluble Granules (SG) Using Other Crystal Forms of Emamectin Benzoate Mentioned in U.S. Pat. No. 6,486,195

The procedure in Example 5 was repeated by using emamectin benzoate crystalline forms A and B mentioned in U.S. Pat. No. 6,486,195.

EXAMPLE 7

Comparison of the Stability of Formulation Having Different Crystalline Forms

SG samples prepared in Examples 5 and 6 were diluted with water and their residues were compared by passing through the wet sieve. The results are tabulated in Table 6.

TABLE 6

| | Residue | |
|---|---|---|
| Sample | Dilution factor 100 | Dilution factor 1000 |
| Crystalline forms A | +++ | +++++ |
| Crystalline forms B | ++++ | ++++ |
| Crystalline forms V | No residue | No residue |

Remark: "+" means small amount of residue, "+++++" means a lot of residue

It is surprising to find that the crystalline modification V of emamectin benzoate is extremely stable after dilution. It has a reduced tendency to aggregate and recrystallized after dilution compared to other crystal forms. For these reasons, it is highly suitable for preparing commercial formulations.

The invention claimed is:

1. A crystalline modification V of emamectin benzoate, exhibiting at least 3 of the following reflexes in an X-ray powder diffractogram recorded using Cu—Kα radiation at 25° C.:

$$2\theta = 4.34 \pm 0.2 \tag{1}$$

$$2\theta = 10.58 \pm 0.2 \tag{2}$$

$$2\theta = 12.32 \pm 0.2 \tag{3}$$

$$2\theta = 15.19 \pm 0.2 \tag{4}$$

$$2\theta = 18.57 \pm 0.2 \tag{5}$$

$$2\theta = 20.41 \pm 0.2 \tag{6}$$

2. The crystalline modification V of emamectin benzoate according to claim 1 exhibiting at least four of said reflexes.

3. The crystalline modification V of emamectin benzoate according to claim 2 exhibiting at least five of said reflexes.

4. The crystalline modification V of emamectin benzoate according to claim 3 exhibiting all six of said reflexes.

5. The crystalline modification V of emamectin benzoate according to claim 1 exhibiting IR spectrum with the following bands at 2970.62 $^{-1}$ and 2934.02 cm$^{-1}$.

6. The crystalline modification V of emamectin benzoate according to claim 1 having a melting endotherm with a peak temperature of 147.77° C. and an extrapolated onset temperature of 142.79° C.

7. A process for the preparation of the crystalline modification V of emamectin benzoate crystal according to claim 1, comprising:
   i) preparing a solution of a solid form of emamectin benzoate in a solvent; wherein solvent comprises ethyl acetate and n-hexane;
   ii) effecting crystallization of emamectin benzoate from the solution; and
   iii) isolating the crystalline modification V of emamectin benzoate crystal formed.

8. The process according to claim 7, wherein ethyl acetate and n-hexane are present in the solvent in a ratio of from 5:1 to 1:5.

9. The process according to claim 8, wherein ethyl acetate and n-hexane are present in the solvent in a ratio of from 4:1 to 1:4.

10. The process according to claim 9, wherein ethyl acetate and n-hexane are present in the solvent in a ratio of about 1:4.

11. A pesticidal composition comprising the crystalline modification V of emamectin benzoate according to claim 1 and at least one additive.

12. The composition in claim 11 in form of suspension concentrates, oil-based suspension concentrates, soluble granules, dispersible concentrates, emulsifiable concentrates (emulsion concentrates), emulsion seed dressings, suspension seed dressings, granules, microgranules, suspoemulsions, water-soluble granules, water-soluble concentrates and water dispersible granules.

13. The composition of claims 11, wherein the additive includes at least one component selected from the group consisting of an extender, solvent or diluent, colorant, wetting agent, dispersant, emulsifier, antifoam, thickener, and water.

14. The composition according to claim 13, wherein the extender is tetrahydrofurfuryl alcohol.

15. The composition according to claim 13, wherein the colorant is FD&C Blue No. 1.

16. The composition according to claim 13, wherein the wetting agent is POE-20 sorbitan monostearate ethoxylate.

17. The composition according to claim 13, wherein the dispersant is nonionic or anionic dispersants, or mixtures of nonionic and anionic dispersants.

18. The composition according to claim 17, wherein the nonionic dispersant is ethylene oxide-propylene oxide block polymers, alkylphenol polyglycol ethers, tristyrylphenol polyglycol ethers, and their phosphated or sulphated derivatives, tristyrylphenol ethoxylates or vinyl acetate/vinylpyrrolidone copolymer.

19. The composition according to claim 17, wherein the anionic dispersant is lignosulphonates, polyacrylic salts or arylsulphonate-formaldehyde condensates.

20. A method for combatting insects, nematodes and plant parasites comprising applying a crystalline modification of Emamectin benzoate according to claim 1, or a composition thereof.

21. The method according to claim 20, wherein the insects, nematodes and plant parasites are selected from the group consisting of *Tribolium* sp., *Tenebrio* sp., (for stored grains), spider mites (*Tetranychus* sp.), aphids (*Acyrthiosiphon* sp.), migratory orthopterans, such as locusts and immature stages of insects living on plant tissue of agricultural plants, southern army worm and Mexican bean beetle larvae, pine coneworm (*Dioryctria* spp.), pine cone seed bug (suppression of *Leptoglossus* and *Tetyra* spp. in the year of treatment), aphid, bagworm, fall webworm, Japanese beetle, gypsy moth, mimosa webworm, oak, tussock moth, leafminers (such as Lepidoptera, coleoptera, pine needle scale, red palm mite, sawfly (such as elm, pine), tent caterpillars (such as Eastern, Forest, Pacific, and Western), western spruce, budworm, winter moth, flatheaded borers (such as adult and larvae of bronze birch borer, emerald ash borer and two-lined chestnut borer), clearwing borers (such as ash and sequoia pine pitch tube moth), ambrosia beetles, round-headed borers (including asian longhorn beetles), scolytids (bark beetles) lps engraver beetles, mountain pine beetle, southern pine beetle, spruce beetle, western pine beetle, cynipid gall wasps including black oak gall, pinewood nematode, lilac borer, ash borer (*Podosesia syringae*) and *Meloidogyne* sp.

* * * * *